United States Patent [19]

Metzger et al.

[11] 3,972,910
[45] Aug. 3, 1976

[54] PREPARATION OF A CHLORINATED DIISOCYANATE

[75] Inventors: Sidney H. Metzger, Leverkusen, Germany; Marvin L. Kaufman, Somerville, N.J.; John E. Over, Pittsburgh, Pa.

[73] Assignee: Bayer Aktiengesellschaft, Leverkusen, Germany

[22] Filed: July 7, 1975

[21] Appl. No.: 594,131

Related U.S. Application Data

[60] Division of Ser. No. 53,710, July 9, 1970, abandoned, which is a continuation of Ser. No. 688,363, Dec. 6, 1967, abandoned.

[52] U.S. Cl. .................... 260/453 PH; 260/2.5 AQ; 260/2.5 AT; 260/77.5 AT; 260/453 AR; 260/573; 260/578
[51] Int. Cl.² ............. C07C 118/02; C07C 119/048
[58] Field of Search ............. 260/453 AR, 453 PH, 260/453 P, 578

[56] References Cited
UNITED STATES PATENTS

| | | | |
|---|---|---|---|
| 3,305,574 | 2/1967 | Zecher et al. | 260/453 |
| 3,497,542 | 2/1970 | Gardner et al. | 260/453 |

*Primary Examiner*—Lewis Gotts
*Assistant Examiner*—Dolph H. Torrence
*Attorney, Agent, or Firm*—Joseph C. Gil; Gene Harsh

[57] ABSTRACT

A process for the preparation of compounds represented by the formula

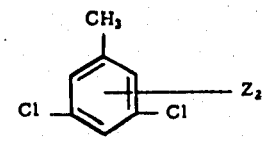

wherein Z is

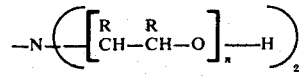

wherein R' and R' are hydrogen, alkyl or aryl and $n$ is 0 or a positive integer, which compounds are particularly useful as chain extenders or in preparing isocyanates or polyols to be used in the production of polyurethane plastics.

1 Claim, No Drawings

PREPARATION OF A CHLORINATED DIISOCYANATE

This is a division of application Ser. No. 53,710 filed July 9, 1970, now abandoned, which application, in turn, is a continuation of co-pending application Ser. No. 688,363, filed Dec. 6, 1967, now abandoned and relates to compounds based on toluene which are substituted with chlorine and nitrogen and more particularly to 2,4- or 2,6-diamino 3,5-dichloro toluene and alkoxylated derivatives.

The direct bromination of ring carbon atoms of 2,4- or 2,6-toluene diamine has been reported but it has not been possible heretofore to prepare chlorinated 2,4- or 2,6-toluene diamine where the chlorine is bonded directly to a ring carbon atom. The chlorine attacks the amino compound and a variety of useless by-products results.

It is therefore an object of this invention to provide compunds, including polymers, which are based on toluene and which contain amino groups and chlorine bonded to ring carbon atoms of the toluene ring. Another object of this invention is to provide processes for the preparation of these compounds. A further object is to provide polyether polyols and a process for the preparation thereof. Another object is to provide amines and processes for the preparation thereof. Still another object is to provide chain-extending agents for polyurethane plastics.

The foregoing objects and others which will become apparent from the following description are accomplished, generally speaking, by providing compounds having the formula

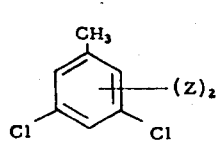

wherein Z is —NH$_2$ or

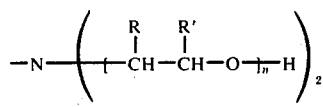

wherein R and R' are hydrogen, alkyl or aryl, $n$ is 0 or a positive integer and there is at least one

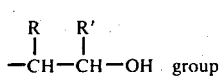 group on each nitrogen atom. The molecule may contain other compatible substituents such as nitro, alkoxy, alkyl, aryl and the like.

Thus the invention provides for amines such as

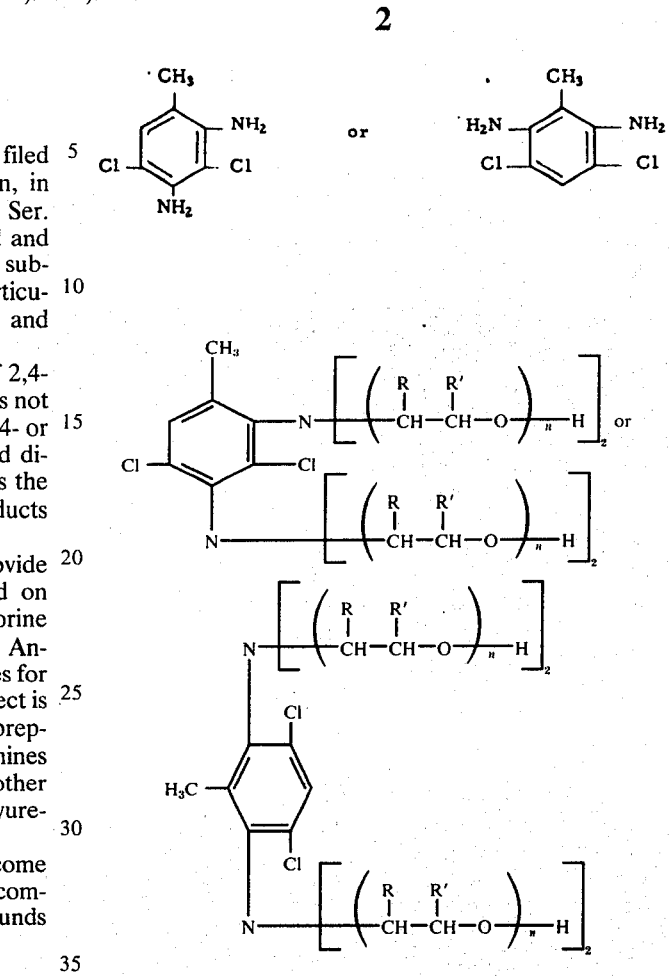

wherein R and R' are the same or different and are hydrogen, alkyl or aryl and $n$ is 0 or a positive integer with the proviso that $n$ is a positive integer on different nitrogen atoms at least twice in the molecule.

The preparation of the compounds of the invention may begin for example, with the known and commercially available compounds 2,4-and/or 2,6-toluene diamine. In this method the toluene ring is chlorinated to obtain one of the new compositions of the invention. It is essential to the process that 2,4- and/or 2,6-toluene diamine is reacted with N-chlorosuccinimide, t-butyl-hypochlorite, or the like as the chlorinating agent.

The reaction can be illustrated with 2,4-toluene diamine and N-chlorosuccinimide as follows:

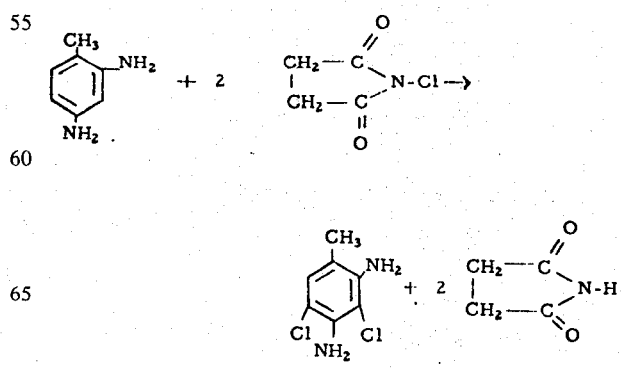

This method is preferably carried out under substantially anhydrous conditions by adding the halogenation agent to the 2,4- and/or 2,6-toluene diamine which has preferably been dissolved in an inert organic solvent such as benzene, dioxane, tetrahydrofuran, carbon tetrachloride, cyclohexane, chlorobenzene and the like. The reaction is preferably carried out at a temperature of 10°C. to 90°C. The product 3,5-dihalo-2,4- and/or 2,6-toluene diamine can be taken up in C Cl$_4$ and recrystallized.

The resulting amine can be phosgenated to prepare a halogenated organic diisocyanate. In this preparation the amines prepared as set forth above are dissolved in an inert organic solvent such as benzene, toluene, ortho-dichlorobenzene, chlorobenzene, the diethyl ether of diethylene glycol, the diethyl ether of triethylene glycol or the like. The solution is preferably cooled to a temperature of about −10°C. to about 5°C. and a cold phosgene solution, usually in the same solvent as was used to dissolve the amine, is introduced while maintaining the temperature below 5°C. The temperature of the fine slurry which results is allowed to rise to about 20°C. while stirring and adding further phosgene. With continuous addition of phosgene the reaction temperature is gradually increased to about 100°C. The reaction mixture clears and the resulting isocyanate, after purging all phosgene from the reaction mixture, can be removed by distillation.

The amines disclosed above can be used to prepare polyethers which are especially useful for the preparation of a polyurethane foam having improved flame resistance. The polyethers may be prepared by reacting the amines with one or more alkylene oxides, if desired sequentially. The polyether of the invention may be represented by the general formula

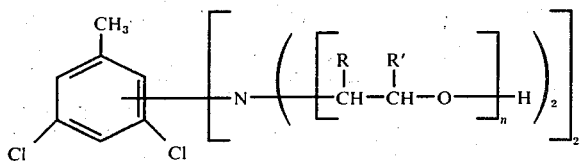

wherein $n$ is 0 or a positive integer preferably 1 – 100 and most preferably of 1 to 8, with the proviso that each nitrogen atom in the molecule carries at least one

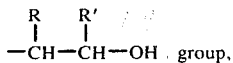 group,

R and R' are the same or different and represent hydrogen, alkyl or aryl as illustrated by the alkylene oxide starting materials set forth below.

Also, in accordance herewith the products resulting from the condensation of the hydroxyl groups of each alkylene oxide radical, which reacts with each hydrogen of the amino groups, with further amounts of alkylene oxides whether they be the same or different is within the contemplated scope of this invention. Thus, polyethers are formed where an alkylene oxide is reacted equivalent for equivalent with the amino hydrogen atoms of the amine and this material is further condensed with more alkylene oxide. The alkylene oxide adducts of the invention are useful as solvents, non-ionic detergents and as valuable intermediates in the preparation of foams. Because of their polyfunctional nature, the compounds are particularly suited for reaction with diisocyanates in the preparation of rigid foams. The adducts containing amino groups are particularly suitable for sprayed urethane foams because of the speed with which these materials set up. Such foams are useful in covering the underside of horizontal surfaces where it is difficult to maintain the sprayed material in position.

The compositions in accordance with this invention are prepared by reacting at least two mols of an alkylene oxide with the amine or mixture of amines as disclosed above. Depending upon the quantity based on an equivalent ratio of the alkylene oxide used in the reaction, the number of the hydrogen atoms on the nitrogen atoms which will be replaced by the alkylene oxide residue is determined. By alkylene oxide residue is meant a radical having the formula

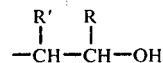

wherein R and R' are hydrogen, alkyl or aryl. The reaction between the amine and the alkylene oxide can be conducted in the presence of a suitable inert solvent in which the amine is slurried or dissolved. The alkylene oxide is then introduced with agitation of the entire body which is preferably heated to a temperature of about 90°C. to about 170°C. The reaction may be carried out under atmospheric or super-atmospheric pressure and to the extent required any exothermic heat can be removed by any conventional heat transfer means. Any suitable solvent which permits a sufficiently high reaction temperature such as toluene, xylylene, diethyl carbitol, dibutyl carbitol, dibutyl ether or the like can be used in conducting the reaction.

Any suitable alkylene oxide or mixture of alkylene oxides can be used in the preparation of the compositions in accordance with this invention such as, for example, ethylene oxide, 1,2-propylene oxide, styrene oxide, 1,2-butylene oxide, 1,2-hexylene oxide, 1,2-heptylene oxide, 2,3-butylene oxide, 3,4-hexylene oxide and the like.

The amount of alkylene oxide used is determined by the average molecular weight of the product desired. For adducts described herein which have utility as intermediates in the preparation of foams, the molecular weights based on the hydroxyl value can range from about 300 to about 10,000 or more. To obtain such products having the desired molecular weight, the amine is treated with an alkylene oxide in accordance with the procedure set forth above and in the ratios desired if less than all of the active hydrogen atoms on the nitrogen atoms are replaced. Where higher molecular weight compounds are desired the alkylene oxide is further reacted with the hydroxyl groups present after reaction of one equivalent of an alkylene oxide with each hydrogen on the nitrogen atoms. The quantity of alkylene oxide reacted with each hydroxyl group of each product can range from 1 to about 100 mols or more. In the second instance that is, where the alkylene oxides are reacted with hydroxyl groups rather than with the amino groups, it is desirable that a catalyst be present in order to promote this reaction. Any suitable catalyst can be used, however, it is preferred to use alkaline catalyst such as, for example, alkali metal catalysts including sodium hydroxide, potassium hydroxide, potassium t-butoxide and the like. The amount of catalyst employed is generally in the range of 0.002 to 2.0 percent by weight based on the total amount of reactants including the alkylene oxide or mixtures thereof appearing in the reaction product. Thus in accordance with the formula represented above the value of n can range from 0 to 100 or more must equal at least 1 at least twice in the molecule. In the first step of the procedure that is, wherein an alkylene oxide is reacted with amino groups no catalyst is necessary however when conducting the reaction in order to prepare a polyether it is preferred to utilize a catalyst as stated above. The catalyst may be added either initially or after the formation of the reaction product of amino groups with alkylene oxides.

The compositions in accordance with this invention also include block polymers wherein initially one alkylene oxide is reacted with the amine and then subsequently in the presence of a catalyst, a different alkylene oxide is reacted with the product prepared from the first reaction. An example of this would be where propylene oxide is first reacted with all of the amino groups present and then subsequently ethylene oxide is reacted with hydroxyl groups formed by the reaction of propylene oxide with the amine. Any combination of the above mentioned alkylene oxides may be used. Further, mixed copolymers can be prepared by reacting a mixture of alkylene oxides such as, ethylene oxide and propylene oxide with the amine.

The average molecular weight and reactivity of the alkylene oxide adducts prepared herein can be determined readily by analysis for hydroxyl content. The hydroxyl number is a measure of and is proportional to the hydroxyl concentration per unit weight. The hydroxyl number is defined in terms of milligrams of KOH equivalent per gram of alkylene oxide amine reaction product and is determined by reacting acetic anhydride or phthalic anhydride (in pyridine solution) at refluxing temperature with the hydroxyl groups of the reaction product. The unreacted anhydride and acetic acid or phthalic acid formed are titrated with aqueous sodium hydroxide using phenolphthalein as an indicator. The molecular weight can be readily calculated from the hydroxyl number by using the formula:

$$M.W. = \frac{\text{Functionality} \times 1000 \times 56.1}{\text{Hydroxyl No.}}$$

where Functionality is defined as the number of reactive hydroxyl groups per molecule.

In the preparation of cellular polyurethanes utilizing the alkylene oxide adducts of the amine any suitable blowing agent may be used which causes the reaction mixture to expand by the generation of gas during the isocyanate polyaddition reaction. The blowing agent may be water which reacts with isocyanates to produce carbon dioxide, a temperature sensitive blowing agent such as, for example, a halohydrocarbon including trichlorofluoromethane dichlorodichloromethane, trichlorotrifluoroethane, dichlorodifluoromethane and the like, and alkane such as butane, hexane, heptane and the like, methylene chloride or any other suitable blowing agent and mixtures thereof.

Any suitable organic polyisocyanate may be used to react with the resulting polyol such as, for example, ethylene diisocyanate, propylene diisocyanate, tetramethylene disocyanate, pentamethylne diisocyanate, octamethylene diisocyanate, undecamethylene diisocyanate, dodecamethylene diisocyanate, 3,3'-diisocyanato dipropylether, and so forth: cyclopentylene-1,3-diisocyanate, cyclohexylene-1,4-diisocyanate, 2,4-tolylene diisocyanate, 2,6-tolylene diisocyanate and mixtures of 2,4-and 2,6-tolylene diisocyanate, xylene-1,4-diisocyanate, xylylene-1,3-diisocyanate, 4,4'-diphenylmethane diisocyanate, 2-nitrodiphenyl-4,4'-diisocyanate 4,4'-diphenylpropane diisocyanate, p-isocyanato benzyl isocyanate, m-phenylene diisocyanate, p-phenylene diisocyanate, naphthylene-1,4-diisocyanate, naphthylene-1,5-diisocyanate, furfurylidene diisocyanate, p,p',p''-triphenylmethane triisocyanate, diphenyl-4,6,4'-triisocyanate, and the like. In addition one may use the organic diisocyanates disclosed above, i.e. 2,4- and/or 2,6-diisocyanato-3,5-dihalo-toluenes. Also suitable are crude polyisocyanates such as crude 4,4'-diphenylmethane diisocyanate which is generally referred to as polyaryl alkylene polyisocyanate. Any such compound including those disclosed in U.S. Pat. No. 2,683,730 may also be used in the process of this invention. In addition to the reactants set forth above, other known accelerators, stabilizers, emulsifiers and the like may be incorporated into the reaction mixture to achieve the results currently attributed to them.

The cellular polyurethane in accordance with this invention are particularly suitable in the manufacture of rigid polyurethane foams which find application in sound and heat insulation, curtain wall constructions, for filling large volumes such as airplane wings and the like.

The amines may also be used as chain-extenders for polyurethane plastics where amine chain-extenders are needed. They have the advantage of improving the casting time for amine extended polymers.

The compounds of the invention are useful as set forth above, i.e. to prepare amines, isocyanates and polyols which can be used to prepare polyurethane plastics with such final end uses as gear wheels, cushions, insulation in the walls of dwellings, etc.

The invention is further illustrated but not limited by the following examples in which parts are by weight unless otherwise specified

EXAMPLE 1

In a 500 cc., 3-necked flask, equipped with a stirrer, thermometer, condenser and nitrogen inlet was charged 12,2 g. (0.1 mol) of 2,4-toluene diamine and 300 cc. of dry benzene. To the stirred solution was added 26.7 g. (0.2 mol) of N-chloro-succinimide (recrystallized) in four equal increments at 53°–78°C. over a period of about 3.5 hours. Benzene insoluble products were removed by filtration and the filtrate was stripped in vacuo. The residue was taken up in carbon tetrachloride and filtered. the carbon tetrachloride solution was concentrated and allowed to cool, whereupon large brown needles (2,4 g.) crystallized m.p. 133°–34°C. Sublimation in vacuo gave pure white crystals, m.p. 134°–35°C.

Analysis: Calculated for dicholoro toluene diamine: C, 43.9; H, 4.19; N, 14.67; Cl, 37.2. Found: C, 43.79; H, 3.78; N, 14.84; Cl, 37.25.

The structure of the compound is established by NMR to correspond to 3,5-dichloro-2,4-diamino toluene.

EXAMPLE 2

In the same equipment as Example 1 was charged 12.2 g. (0.1 mol of 80/20 2,4-/2,6-toluene diamine, and 150 cc. of dry dioxane. At 77°–82°C., with stirring a solution of 26.6 g. (0.2 mol) of NCS in 150 cc. of dioxane was gradually added over a period of about 40 minutes. Heating was continued for one hour. The reaction mixture was filtered to remove insolubles, and all dioxane was stripped from the filtrate. The residue was taken up in carbon tetrachloride and filtered. From the carbon tetrachloride solution was obtained by crystallization (brown needles) 7.0 g. of the 3,5-dichloro derivatives of mixture of 2,4- and 2,6-toluene diamine, m.p. 114°–121°C.

EXAMPLE 3

Into a stirred autoclave is charged 191 parts (1 mol) of the amine prepared as in Example 1. The amine is heated to 140°C. whereupon the addition of propylene oxide is started. At 130°–140°C. 238 g. (4.1 mols) of propylene oxide is slowly pumped in over a period of two hours. Maximum pressure reached is 110 psig. At the end of the propylene oxide addition stirring and heating are continued for one hour, then the pressure is relieved and a vacuum pulled on the hot stirred mixture to remove any propylene oxide remaining or low-boiling by-products. The product is a low-melting solid with an hydroxyl number of 529.

EXAMPLE 4

Example 3 is repeated, but using the mixture of dichlorinated amines as obtained in Example 2.

The following example is offered for the purpose of demonstrating that direct chlorination of 2,4-toluene diamine is not possible.

EXAMPLE 5

A 500 ml. round bottom flask fitted with stirrer dry-ice acetone condenser thermometer and gas inlet was charged with 12.2 g. (0.1 mol) 2,4-toluene diamine dissolved in 300 ml. of glacial acetic acid. The flask was cooled to approximately 15°C. and $Cl_2$ bubbled into the solution. $Cl_2$ was taken up immediately by the solution and the addition was continued until $Cl_2$ began to reflux. The reaction mixture was then purged with $N_2$ and allowed to stand overnight during which time a precipitate formed. The precipitate was filtered off and washed with toluene and the filtrate and wash were combined and taken to dryness using a rotary evaporator. The infrared spectra of the two products were essentially identical. The NMR spectra showed that the protons of the methyl group were still present and that protons which could be assigned to the $NH_3$ group also were present. Other multiplets were also present in the spectra but were not assigned to any structure. No dichloro toluene diamine was detected. The reaction was also carried out in acetic acid saturated with HCl. The same product as above was obtained. The reaction was also carried out in aqueous solution and in methyl alcohol and again no dichloro-toluene diamine was obtained.

It is to be understood that the foregoing working examples are given for the purpose of illustration and that any other suitable halogenated agent catalyst phosgenation procedure alkylene oxide or the like can be used provided that the teachings of this disclosure are followed.

Although the invention has been described in considerable detail in the foregoing for the purpose of illustration it is to be understood that such detail is solely for this purpose and that variations can be made by those skilled in the art without departing from the spirit and scope of the invention.

What is claimed is:

1. A method of preparing a chlorinated diisocyanate comprising the steps:

A. reacting 2,4- or 2,6-toluene diamine or mixtures thereof which are dissolved in an inert organic solvent with a chlorinating agent selected from the group consisting of N-chlorosuccinimide and t-chlorobutylhypochlorite at a temperature of from about 10°C to about 90°C, thereby forming a chlorinated diamine having the general formula

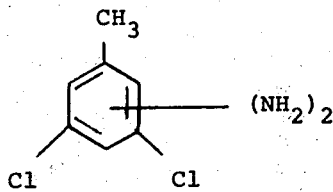

and

B. reacting said diamine with phosgene.

* * * * *